US012745928B2

(12) United States Patent
Vanpoucke

(10) Patent No.: US 12,745,928 B2
(45) Date of Patent: Sep. 29, 2026

(54) SCORING SPEECH AUDIOMETRY

(71) Applicant: Cochlear Limited, Macquarie University (AU)

(72) Inventor: Filiep J. Vanpoucke, Huldenberg (BE)

(73) Assignee: Cochlear Limited, Macquarie University (AU)

( * ) Notice: Subject to any disclaimer, the term of this patent is extended or adjusted under 35 U.S.C. 154(b) by 987 days.

(21) Appl. No.: 17/770,901

(22) PCT Filed: Nov. 18, 2020

(86) PCT No.: PCT/IB2020/000952
§ 371 (c)(1),
(2) Date: Apr. 21, 2022

(87) PCT Pub. No.: WO2021/099834
PCT Pub. Date: May 27, 2021

(65) Prior Publication Data

US 2022/0386902 A1 Dec. 8, 2022

Related U.S. Application Data

(60) Provisional application No. 62/938,572, filed on Nov. 21, 2019.

(51) Int. Cl.
*A61B 5/12* (2006.01)

(52) U.S. Cl.
CPC .................................... *A61B 5/123* (2013.01)

(58) Field of Classification Search
None
See application file for complete search history.

(56) References Cited

U.S. PATENT DOCUMENTS 6,302,697 B1 10/2001 Tallal et al.
6,435,877 B2 8/2002 Wasowicz
(Continued)

FOREIGN PATENT DOCUMENTS

JP 2014-176582 A 9/2014
KR 10-2006-0097404 A 9/2006
(Continued)

OTHER PUBLICATIONS

De Graaff, Feike, et al. "The development of remote speech recognition tests for adult cochlear implant users: the effect of presentation mode of the noise and a reliable method to deliver sound in home environments." Audiology and Neurotology 21.Suppl. 1 (2016): 48-54. (Year: 2016).*
(Continued)

*Primary Examiner* — Benjamin S Melhus
(74) *Attorney, Agent, or Firm* — Edell, Shapiro & Finnan, LLC

(57) ABSTRACT

This application relates to audiometric testing techniques. An example implementation is based on audibly providing a target word to a user and receiving a response of what the user audibly perceived in text form. The text is then converted into phonemes and compared with phonemes of the target word. In many examples, the process is repeated for multiple target words. The resulting comparison data can be used to determine the user's ability to hear and can be the basis for one or more treatment actions if the results reveal the user may suffer from hearing loss. The treatment actions can include providing the user with a hearing device or modifying an existing hearing device of the user.

20 Claims, 10 Drawing Sheets

(56) References Cited

U.S. PATENT DOCUMENTS

| | | | | |
|---|---|---|---|---|
| 6,584,440 | B2 | 6/2003 | Litovsky | |
| 7,143,031 | B1 * | 11/2006 | Ahroon | A61B 5/121 704/224 |
| 7,149,684 | B1 | 12/2006 | Ahroon | |
| 7,206,416 | B2 | 4/2007 | Krause et al. | |
| 7,676,372 | B1 | 3/2010 | Oba | |
| 8,433,568 | B2 | 4/2013 | Krause et al. | |
| 8,529,464 | B2 | 9/2013 | Wasden et al. | |
| 8,612,011 | B2 | 12/2013 | Seligman | |
| 8,693,639 | B2 | 4/2014 | Rottier et al. | |
| 8,844,358 | B2 | 9/2014 | Chalupper et al. | |
| 9,131,876 | B2 | 9/2015 | Koo et al. | |
| 9,420,381 | B2 | 8/2016 | Choi et al. | |
| 9,794,705 | B2 | 10/2017 | Wiggins et al. | |
| 9,833,174 | B2 | 12/2017 | Bochner et al. | |
| 9,844,326 | B2 | 12/2017 | Bamerjee et al. | |
| 10,078,631 | B2 | 9/2018 | Bellegarda | |
| 10,129,671 | B2 | 11/2018 | Krause et al. | |
| 10,198,964 | B2 | 2/2019 | Reed et al. | |
| 10,368,154 | B2 | 7/2019 | Blau et al. | |
| 2011/0087130 | A1 * | 4/2011 | Cheema | A61B 5/121 600/559 |
| 2012/0109630 | A1 | 5/2012 | Badino et al. | |
| 2015/0127347 | A1 | 5/2015 | Tjalve et al. | |
| 2016/0045142 | A1 | 2/2016 | Morita et al. | |
| 2018/0012511 | A1 | 1/2018 | Reed et al. | |
| 2018/0125415 | A1 * | 5/2018 | Reed | A61B 5/4803 |
| 2019/0320946 | A1 * | 10/2019 | Bromwich | A61B 5/7475 |
| 2021/0264937 | A1 * | 8/2021 | Oliver | G10L 15/20 |

FOREIGN PATENT DOCUMENTS

| | | | |
|---|---|---|---|
| KR | 10-2011-0090066 | A | 8/2011 |
| WO | 2001026272 | A2 | 4/2001 |
| WO | 2019215459 | A1 | 11/2019 |

OTHER PUBLICATIONS

International Search Report and Written Opinion in counterpart International Application No. PCT/US2020/000952, mailed Apr. 5, 2021, 10 pages.

Wikipedia, "Levenshtein distance", https://en.wikipedia.org/wiki/Levenshtein_distance, May 2019, 8 pages.

InternationalPhoneticAlphabet.org, "IPA Chart With Sounds", https://www.internationalphoneticalphabet.org/ipa-sounds/ipa-chart-with-sounds/, May 2019, 6 pages.

Moran, Steven & McCloy, Daniel, "PHOIBLE 2.0.", https://phoible.org/inventories, May 2019, 5 pages.

Wikipedia, "ARPABET", https://en.wikipedia.org/wiki/ARPABET, May 2019, 4 pages.

VoxForge, "What is G2P?", http://www.voxforge.org/home/docs/faq/faq/what-is-g2p, May 2019, 2 pages.

Francart, Tom et al., "Automatic testing of speech recognition", https://www.ncbi.nlm.nih.gov/pubmed/19219692, May 2019, 1 page.

Extended European Search Report in counterpart European Application No. 20889255.4-1113, mailed Nov. 6, 2023, 5 pages.

* cited by examiner

501

502

| 510 | 520 | 530 | 540 | 550 | 560 | 570 | 580 |
|---|---|---|---|---|---|---|---|
| File | Target Word | User Response | Target Word Phonemes | User Response Phonemes | Phoneme Score | Word Score | Time (ms) |
| 021 | Patch | Patch | [[P, AE, CH]] | [[P, AE, CH]] | [1, 1, 1] | 3 | 623 |
| 045 | Thin | Hint | [[TH, IH, N]] | [[HH, IH, N, T]] | [0, 1, 0] | 1 | 1603 |
| 027 | Route | Wrote | [[R,AW,T][R,UW,T]] | [[R,OW,T]] | [1, 0, 1] | 2 | 2505 |
| 043 | Dime | Dime | [[D, AY, M]] | [[D, AY, M]] | [1, 1, 1] | 3 | 471 |
| 007 | Sun | Sun | [[S, AH ,N]] | [[S, AH ,N]] | [1, 1, 1] | 3 | 589 |
| 004 | Bean | Been | [[B, IY, N]] | [[B, AH, N]] | [1, 0, 1] | 2 | 1833 |
| 034 | Wish | With | [[W, IH, SH]] | [[W, IH, TH] [W, IH, DH]] | [1, 1, 0] | 2 | 189 |
| 011 | Home | Hope | [[HH, OW, M]] | [[HH, OW, P]] | [1, 1, 1] | 2 | 1101 |
| 006 | Ditch | | [[D, IH, CH]] | [] | [0, 0, 0] | 0 | 2790 |
| 002 | Name | Name | [[N, EY, M]] | [[N, EY, M]] | [1, 1, 1] | 3 | 734 |

FIG. 5B

Phoneme Analysis 590

592

| Phoneme | Count | Incorrect |
|---|---|---|
| AE | 1 | 0 |
| AH | 2 | 1 |
| AY | 1 | 0 |
| B | 1 | 0 |
| CH | 2 | 1 |
| D | 2 | 1 |
| EY | 1 | 0 |
| HH | 2 | 1 |
| IH | 3 | 1 |
| M | 2 | 0 |
| M | 4 | 0 |
| OW | 2 | 1 |
| P | 2 | 0 |
| R | 1 | 0 |
| S | 1 | 0 |
| T | 2 | 1 |
| TH | 1 | 1 |
| W | 1 | 0 |

594

| | |
|---|---|
| Phoneme Score | [28, 27, 27] |
| Total Word Score | 21 |
| Total Percent | 70% |

FIG. 5C

SCORING SPEECH AUDIOMETRY

This application is being filed on Nov. 18, 2020, as a PCT International Patent application and claims priority to and the benefit of U.S. patent Provisional application Ser. No. 62/938,572, filed Nov. 21, 2019, the entire disclosure of which is incorporated by reference in its entirety.

BACKGROUND

Audiometry relates to the measurement of one's hearing. An audiometric test can include measuring a user's reactions to sounds. For instance, a user can listen to short words in a sound booth and repeat back verbally what the user understood. In an unaided audiometric test, the user's natural hearing (e.g., without augmentation by an auditory device) is tested. In an aided audiometric test, the user's hearing as augmented by an auditory device is tested. The test can be directed to one or both of the user's ears a time. The content of the test can include monosyllabic words, disyllabic words, entire sentences, or take other forms. An audiologist can listen to and score the responses.

SUMMARY

In an example, there is a computer-readable medium storing instructions that, when executed by one or more processors, cause the one or more processors to: select a target word from a plurality of words of an audiometric test; provide test audio of the target word being pronounced; obtain a user response as text data over a user interface; convert the text data into a user response phonetic representation; obtain a target word phonetic representation for the target word; compare the user response phonetic representation and the target word phonetic representation to obtain comparison data; and determine an ability of the user to hear based on the comparison data.

In another example, there is a method comprising: providing, to a user, test audio that includes a target word being pronounced; obtaining a user response from the user; converting the user response into a user response phonetic representation; converting the target word into a target word phonetic representation; comparing the user response phonetic representation and the target word phonetic representation to obtain comparison data; and determine an ability of the user to hear based on the comparison data.

In yet another example, there is a system comprising: a text input component; a sound output component; one or more processors; and memory storing instructions that, when executed by the one or more processors, cause the one or more processors to: provide, via the sound output component, test audio that includes a target word being pronounced; obtain text data from the text input component; converting the text data into a user response phonetic representation; obtaining a target word phonetic representation for the target word; comparing the user response phonetic representation and the target word phonetic representation to obtain comparison data; and determine an ability of the user to hear based on the comparison data.

BRIEF DESCRIPTION OF THE DRAWINGS

The same number represents the same element or same type of element in all drawings.

FIG. 5, which is made up of FIGS. 5A, 5B, and 5C, illustrates example audiometric test results.

FIG. 5B illustrates an example implementation of a results table.

FIG. 5C illustrates an example implementation of phoneme analysis data.

DETAILED DESCRIPTION

This application relates to audiometric testing techniques. For each target word of an audiometric test of one or more target words, a test system can audibly provide a target word to a user and receive a response of what the user audibly perceived. The response can include graphemes (e.g., the orthographic spelling of what the user perceived). The graphemes are then converted into phonemes using, for example, a dictionary or pronunciation rules of a language to produce one or more phoneme representations of the response. Then a comparison can be made between the phonetic representations of the target word and the user response (e.g., using the Levinshtein algorithm to determine a distance therebetween). Where multiple potential phonetic representations exist, multiple comparisons can be made (e.g., each user response representation is compared with each target word representation) and the best matching pair is used.

The results of one or more of the comparisons can be used to determine a phoneme score. Other data in addition to or instead of phoneme scores can be used. Error patterns can be discovered across multiple comparisons of the audiometric test. For example, a person may tend to make particular kinds of errors, such as having trouble hearing vowels, fricatives, or plosives. The resulting data phoneme scores can reflect the user's ability to hear and can be the basis for one or more treatment actions if the results reveal the user may suffer from hearing loss. For instance, the treatment actions can include providing the user with a hearing device or modifying an existing hearing device of the user (e.g., adjust low frequency gains of the device responsive to vowel errors or adjusting the high frequency gains in response to errors with fricatives). Other treatment actions can include the use of rehabilitation exercises, such as playlists of words having sounds that the user had trouble hearing.

As a specific example, the target word can be "dog" and the user's response can be "do". The target word is then converted into three different phonetic pronunciations: /d dɒg g/, /d dɔg g/, /dɑg/, each relating to a different regional pronunciation of the word. The user's response ("do") is then transcribed (e.g., using a grapheme to phoneme system) into three possible phonetic forms: /ddɒ /, /d dɔ / and/do:/. The resulting phonemes can be compared, with the best match being between the target word phonetic representation /d dɒg g/ and the user response phonetic representation /d dɒ /. Comparing the two can result in a phoneme score of 67% (e.g., two of three parts match).

Figure 1:
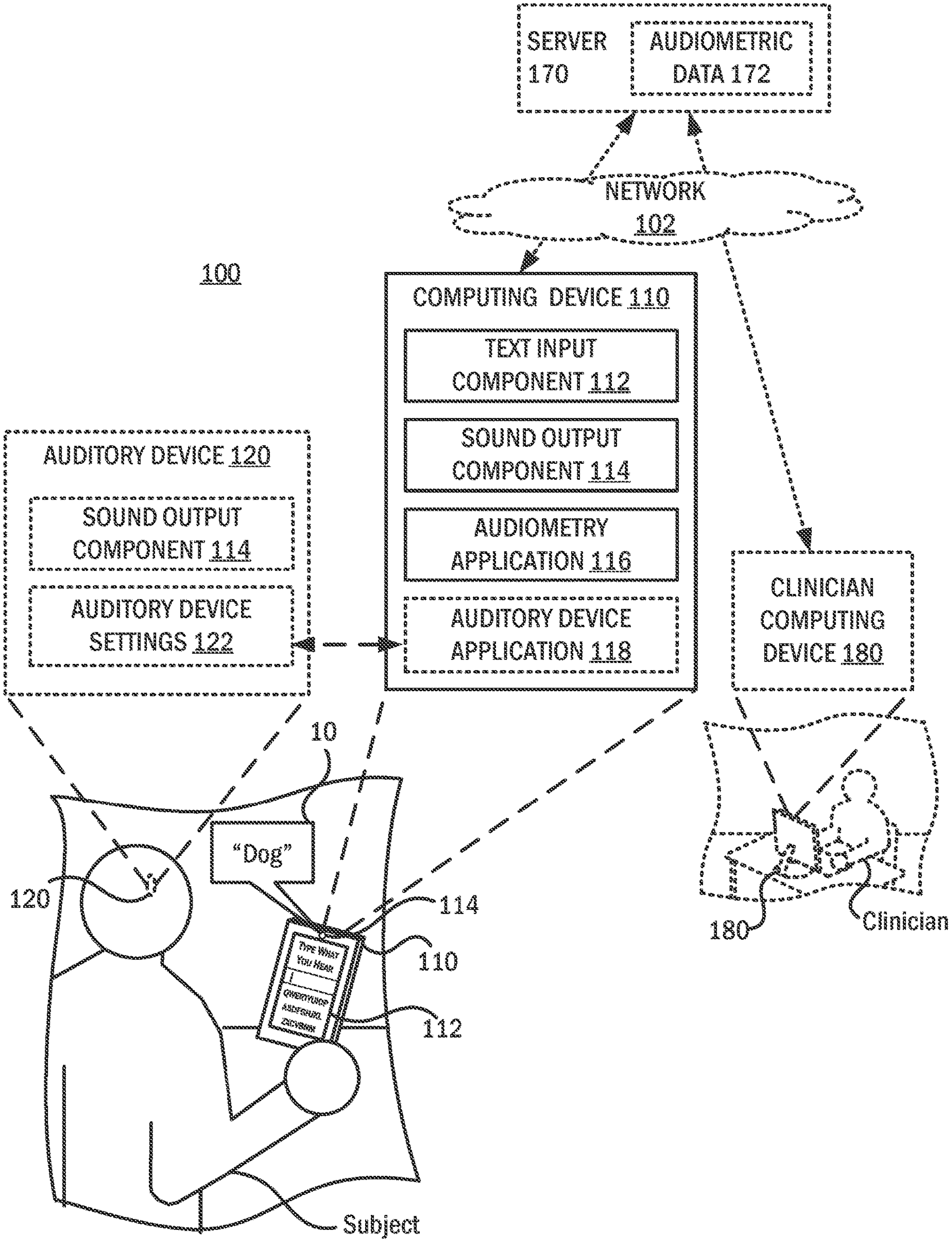
FIG. 1 illustrates an audiometric system for performing one or more audiometric tests.

An example audiometric system for performing audiometric tests is shown in FIG. 1.

Audiometric System

FIG. 1 illustrates an audiometric system 100 for performing one or more audiometric tests for a user. The audiometric system 100 includes a computing device 110 configured to perform the audiometry. The audiometric system 100 can further include a server 170 connected to the computing device 110 via a network 102. The audiometric system 100 can further include a clinician computing device 180. In some examples, the user of the audiometric system 100 can be the recipient of an auditory device 120.

The network 102 is a computer network, such as the Internet, that facilitates the electronic communication of data among computing devices connected to the network 102.

The computing device 110 can be a device having a computer functionality. The computing device 110 can be a consumer computing device owned or primarily used by the user or a parent or caregiver of the user, such as, such as a phone, tablet, laptop computer, desktop computer, consumer augmented reality device, consumer virtual reality device, smart watch, or consumer heart rate monitor, among other devices. In other examples, the computing device 110 can be a device owned or used by an organization, such as a school, clinic, or audiometry service. As illustrated, the computing device 110 can include a text input component 112, a sound output component 114, and an audiometry application 116. Where the user has an auditory device 120, the computing device 110 can include an auditory device application 118. The computing device 110 can include one or more components or functionality described in relation to the computing system 800 of FIG. 8.

The text input component 112 can be a component over which the computing device 110 can receive text data from the user, such as a touchscreen configured to receive touch input (e.g., the computing device 110 can convert the touch input into text data). Where the text input component 112 includes a touchscreen, the text input component 112 can display a virtual keyboard and convert tap or swipe touch input at the keys of the virtual keyboard into text data. In another example, the text input component 112 is one or more buttons (e.g., keys of a keyboard) configured to receive button input and convert the button input into text data. In another example, the text input component 112 is a component (e.g., a microphone) of a speech-to-text system provided by the computing device 110. The computing device 110 can be configured such that applications running on the computing device 110 can receive text input via the text input component 112.

The sound output component 114 can be a component over which the computing device 110 can provide sound output, such as one or more speakers. The sound output component 114 can be a component that cooperates with another device to provide sound output. For instance, the sound output component 114 can be an audio-out port of the computing device 110 or a wireless transmitter (e.g., a BLUETOOTH component) configured to connect to another device that provides audio output (e.g., a speaker, headphones, or a component of the auditory device 120). The computing device 110 can be configured such that applications running on the computing device 110 can provide audio output via the sound output component 114.

The audiometry application 116 can be software that operates on the computing device 110 and causes performance of audiometry operations described herein. In many examples, the audiometry application 116 provides audio output, receives user responses, analyzes the responses, and provides an indication of the user's ability to hear. Example operations performed by the audiometry application are described in FIG. 2. In some examples, the instructions can be obtained as part of a downloadable package, such as may be downloaded from a software distribution platform. In some examples, the audiometry application 116 is a browser via which the server 170 is accessed to provide audiometry functionality (e.g., an audiometric test web app can be provided by the server 170 and accessed by a browser of the computing device 110).

The auditory device application 118 can be software that operates on the computing device 110 and cooperates with the auditory device 120. The auditory device application 118 can be stored as computer-executable instructions in memory of the computing device 110 that, when executed, performs one or more tasks relating to the auditory device application 118. For instance, the auditory device application 118 can control the auditory device 120 (e.g., by modifying the auditory device settings 122 automatically or based on input received at the computing device 110 from the recipient), monitor usage of the auditory device 120, and obtain data from the auditory device 120. The computing device 110 can connect to the auditory device 120 via, for example, a wireless radiofrequency communication protocol (e.g., BLUETOOTH or WI-FI). The auditory device application 118 can transmit or receive data from the auditory device 120 over such a connection. The auditory device application 118 can be used to stream audio to the auditory device 120, such as from a microphone of the computing device 110 or an application running on the computing device 110 (e.g., the audiometry application 116).

The auditory device 120 can be an apparatus relating to the user's sense of hearing. The auditory device 120 can take a variety of forms including a cochlear implant, an electroacoustic device, a percutaneous bone conduction device, a passive transcutaneous bone conduction device, an active transcutaneous bone conduction device, a middle ear device, a totally-implantable auditory device, a tinnitus management device, a mostly-implantable auditory device, an auditory brainstem implant device, a hearing aid, a tooth-anchored hearing device, a personal sound amplification product, other auditory prostheses, and combinations of the foregoing (e.g., binaural systems that include a prosthesis for a first ear of a recipient and a prosthesis of a same or different type for the second ear). Specific example implementations of the auditory device 120 are described in more detail in FIG. 6 (showing a cochlear implant) and FIG. 7 (showing a percutaneous bone conduction device). Technology disclosed herein can be used with sensory devices such as consumer auditory devices (e.g., a hearing aid or a personal sound amplification product). Further, normal hearing people or people with a hearing loss may use an auditory device 120 such as headphones or standard audiometers during a hearing test. As illustrated, the auditory device 120 can include the sound output component 114. The auditory device 120 can operate according to one or more auditory device settings 122.

The auditory device settings 122 can be one or more parameters having values that affect how the auditory device 120 operates. For example, the auditory device 120 can receive audio input from the environment (e.g., using a microphone), convert the audio input into a stimulation signal, and use the stimulation signal to produce stimulation (e.g., vibratory or electrical stimulation) to cause a hearing percept in the user. The auditory device settings 122 can include a map having minimum and maximum stimulation levels for stimulation channels. The map can then be used by the auditory device 120 to control an amount of stimulation provided. Where the auditory device 120 is a cochlear implant, the map can affect which electrodes of the cochlear implant to stimulate and in what amount based on received audio input. In some examples, the auditory device settings 122 include two or more predefined groupings of settings selectable by the recipient. The auditory device settings 122 can also include settings that modify sensory input before the sensory input is converted into a stimulation signal. Such settings can include, for example, particular audio equalizer settings can boost or cut the intensity of audio at various frequencies. In examples, auditory device settings 122 can include a minimum threshold for which received audio input causes stimulation, a maximum threshold for preventing stimulation above a level which would cause discomfort, gain parameters, intensity parameters (e.g., loudness), and compression parameters. The auditory device settings 122 can include settings that affect a dynamic range of stimulation produced by the auditory device 120. As described above, many of auditory device settings 122 affect the physical operation of the auditory device 120, such as how the auditory device 120 provides stimulation to the user in response to audio input received from the environment. Thus modifying the auditory device settings 122 can modify treatment provided by the auditory device 120. Examples of settings, settings modification, and pre-processing for auditory prostheses are described in U.S. Pat. Nos. 9,473,852 and 9,338,567, which are both incorporated herein by reference for any and all purposes.

The server 170 can be a server computing device remote from the computing device 110. The server 170 can include a processing unit and memory, which are described in more detail in FIG. 8. The server 170 can further includes instructions executable to perform one or more of the operations described herein. The server 170 can be communicatively coupled to the computing device 110 via the network 102. The server 170 can be indirectly communicatively coupled to the auditory device 120 through the computing device 110 (e.g., via the auditory device application 118). In certain examples, the computing device 110 can be considered a client device of the server 170. In some examples, the functionality provided by the server 170 or the components thereof can be provided by or located on a device local to the recipient (e.g., the computing device 110 or the auditory device 120). One or both of the auditory device application 118 and the audiometry application 116 can be a client application configured to interact with the server 170. For example, as illustrated, the server 170 can include audiometric data 172, such as audiometric test data usable to provide an audiometric test. The test data can specify the kinds of tests to run, and the data used for those tests. For example, the test data can include audio files of the target words being spoken. The audio files can then be streamed to the computing device 110 or provided as downloads to the computing device 110. In some examples, the audiometric data 172 includes the results of the audiometric tests, such as for review by the clinician via the clinician computing device. In examples, audiometric test processing can be performed at the server. For instance, one or more operations described herein as being performed by the audiometry application 116 on the computing device 110 can be performed at least in part on the server 170.

The clinician computing device 180 can be a computing device used by a clinician. A clinician can be a medical professional, such as an audiologist. In an example, the clinician is a medical professional that provides care or supervision for the user. The clinician computing device 180 includes one or more software programs usable to monitor the audiometric test. For example, responsive to an audiometric test being performed for the user, the results of the test can be provided to the clinician via the clinician computing device 180 for analysis or a decision regarding how to proceed. In some examples, the clinician computing device 180 can be used by the clinician to remotely connect to the computing device 110 to administer the audiometry test.

Method

Figure 2:
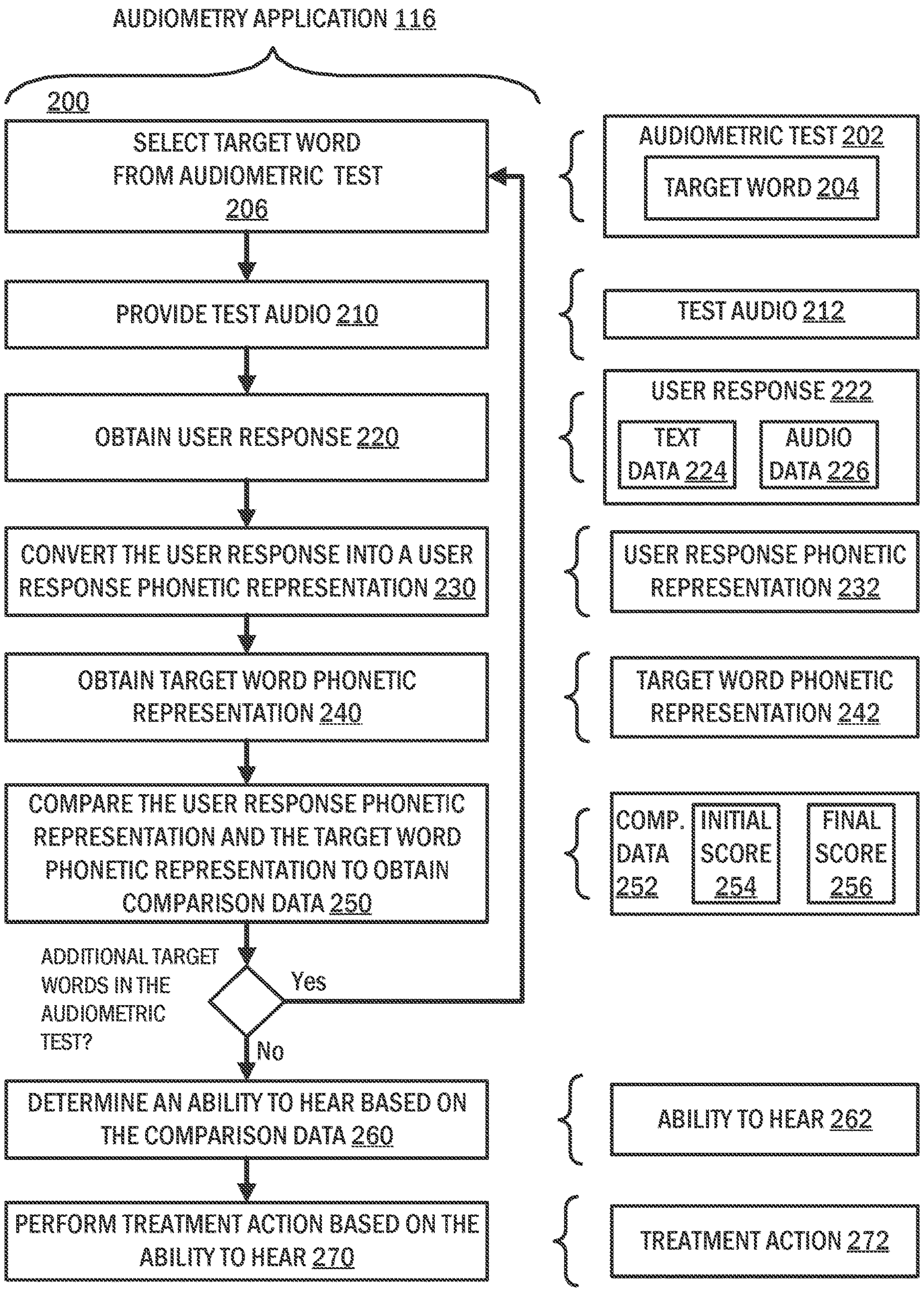
FIG. 2 illustrates a method for conducting an audiometric test.

FIG. 2 illustrates an example method 200 for conducting an audiometric test 202. In some examples, the method 200 can be performed as a result of one or more instructions being executed by one or more processors. For instance, the instructions can be audiometry application instructions stored on a non-transitory computer-readable medium, such as one of the computing device 110.

The audiometric test 202 can be a test of a user's hearing. The audiometric test 202 can take any of a variety of forms. The audiometric test 202 can include a list of target words 204 to be audibly provided to the user. Each target word 204 can be a particular cue to be provided to the user and to which the user provides a response (in many examples, providing an indication of what the user understood the target word to be). For instance, the target word 204 may be a consonant-vowel-consonant (CVC) word, CCVC word, CVCC word, or take another form. A CVC word need not be just a three letter word. Instead, it can be a word having a consonant sound followed by a vowel sound followed by another consonant sound. While referred to herein in the context of a "word", in certain examples, the target word 204 can be a phrase (having multiple words) or parts of a word.

The audiometric test 202 can specify the list of target words 204 in a suitable format, such as a markup language (e.g., XML). In some implementations, there need not be a predefined list of target words 204. In some examples, the content of the list of target words 204 is chosen arbitrarily. In other examples, the list or the contents of the list can be chosen for a specific reason, such as testing specific kinds of words or sounds for which the user has or is thought to have difficulty perceiving. In further examples, an audiologist selects the audiometric test 202 (e.g., remotely from the clinician computing device 180). The target word 204 can be selected from a plurality of target words of the audiometric test 202. The audiometric test 202 can be stored in a variety of locations, such as by being stored locally to the computing device 110 or at the server 170. In examples, the audiometric test 202 is downloaded to the computing device 110 from the server 170.

In examples, the audiometric test 202 can specify other data. For example, the audiometric test 202 can specify one or more complicating factors to add when providing the target words 204. For instance, an audiometric test may add particular complications to the test audio relating to particular conditions (e.g., white noise, brown noise, sounds of one or more conversations occurring, echo, reverberation, distortion, or other effects). The audiometric test 202 can further specify how the target words 204 are provided, such as at a particular volume. Further, there may be multiple different audio files containing the target word 204 (e.g., having a different accent, pronunciation, or vocal characteristics) and the audiometric test 202 can identify particular audio files to be used for the target word 204. In another example the target word 204 can be provided by a text-to-speech system and the audiometric test 202 can specify which text-to-speech system to use or parameters to be used when generating the speech (e.g., vocal characteristics).

In some examples, the method 200 can begin with operation 206.

Operation 206 includes selecting a target word 204 from an audiometric test 202. Selecting the target word 204 can include selecting a first target word 204 of the audiometric test 202 or a next target word 204 of the audiometric test 202. The selection can be in a defined order (e.g., sequentially through a list) or can be selected arbitrarily (e.g., words are selected randomly or pseudorandomly until a total number of words have been used as part of the audiometric test 202). The selecting can include selecting an identifier associated with the target word 204, an audio file associated with the target word 204, or text of the target word 204. Following operation 206, the method 200 can move to operation 210.

Operation 210 includes providing test audio 212. The test audio 212 can include the target word 204 being pronounced. Providing the test audio 212 can include causing sound to be produced based on the test audio. The test audio 212 can be provided using the sound output component 114. For instance, providing the test audio 212 can include providing the test audio 212 using a speaker, headset, or the auditory device 120 to audibly produce the test audio 212. The operation 210 can include obtaining the test audio 212, such as using an identifier of the target word 204. For instance, an identifier of the target word 204 can be used to access a file storing the test audio 212 or stream the test audio from the server 170 (e.g., from the audiometric data 172 stored thereon). In some examples, providing the test audio 212 includes generating the test audio 212. For instance, the computing device 110 can include text-to-speech functionality (e.g., using IOS's AVSpeechUtterance class or ANDROID's textToSpeech API) or a remote computing device providing text-to-speech functionality. The audiometry application 116 can provide text of the target word 204 to a text-to-speech system to cause audio output containing the target word 204 to be produced. In still other examples, a human can provide the test audio 212, such as by being prompted with the target word 204. In some examples, the test audio 212 can be processed (e.g., to have noise or distortion added). Following operation 210, the flow of the method 200 can move to operation 220.

Operation 220 includes obtaining a user response 222 from the user. The user response 222 can be obtained over a user interface. The user response 222 can include text data 224 or audio data 226. The user response 222 can be a response from the user to the test audio 212. In some examples, before, during, or after the providing of the test audio 212, the audiometry application 116 can prompt the user to provide a user response 222 describing what the user perceived or understood from the test audio 212. Obtaining the user response 222 can include providing a user interface over which the user response 222 can be received. For instance, the user interface can include a text input component 112, such as is described in FIG. 1. The operation 220 can include making the text input component 112 available for receiving text data 224 of the user response 222. The operation 220 can include making an audio input component (e.g., a microphone) available for receiving audio data 226 of the user response 222. In some examples, obtaining the user response 222 can include checking the user response 222. The checking can include, for example, determining whether the user response 222 includes a valid word. If the user response 222 includes an invalid word (e.g., a word not contained in a dictionary of the user's language), then the computing device 110 may inform the user that the word is invalid (e.g., indicate that the word is potentially misspelled). In other examples, invalid words may be allowed to be provided as input. Following operation 220, the flow of the method 200 can move to operation 230.

Operation 230 includes converting the user response 222 into a user response phonetic representation 232. For example, where the user response 222 includes text data 224, this operation 230 can include performing a grapheme to phoneme conversion on the text data 224 to generate the user response phonetic representation 232. The user response phonetic representation 232 is a representation of the user response 222 in a phonetic form. For instance, the user response phonetic representation 232 can represent the user response 222 using the ARPABET or IPA phonetic systems. ARPABET includes phonetic transcription codes that represents phonemes and allophones of general American English with distinct sequences of ASCII characters. The IPA is an alphabetic system of phonetic notation based primarily on the Latin alphabet. Other representations or combinations of representations can be used.

In an example, the conversion can be produced using one or more dictionaries. For instance, one or more dictionaries can be searched based on the text data 224 to obtain one or more user response phonetic representations 232. The one or more dictionaries can include, for example, a standard language-specific corpus dictionary (e.g., the CMU phonetic dictionary, which is a U.S. English ARPABET dictionary) or an extension dictionary that can be adjusted (e.g., by an audiologist) to extend or overrule the conversation (e.g., to correct for dialect-specific pronunciations). In an example, a data structure (e.g., a hash table, database, or dictionary data structure) can allow lookup to be performed on text input to produce one or more phonetic representations as output. In addition or instead of using one or more dictionaries, the conversion can be performed using one or more rules. The rules can be symbol substitution rules to convert the text data 224 into a phonetic transcription. For instance, the rules can reflect the standard rules in a particular language for how written form is converted into a spoken form. In some examples, the conversion can first be attempted using the one or more dictionaries and then, if one or more matches are not found in the one or more dictionaries, then conversion can be attempted using the rules.

Where the user response 222 includes audio data 226, converting the user response 222 into a user response phonetic representation 232 can include transcribing the audio data 226 into one or more phonemes to generate the user response phonetic representation 232. For instance, a speech-to-phoneme algorithm can be used. In other examples, the audio data 226 can be transcribed into text data (e.g., using a speech-to-text process) that is then converted into phonemes using the techniques described above.

Following operation 230, the flow of the method 200 can move to operation 240.

Operation 240 includes obtaining a target word phonetic representation 242 for the target word 204. The target word phonetic representation 242 can be obtained in any of a variety of ways. For instance, the target word phonetic representation 242 can be pre-generated and stored in association with the target word 204 as part of the audiometric test 202. In such examples, the target word phonetic representation 242 can be obtained by looking up a stored phonetic representation of the target word 204. In other examples, the target word 204 is generated via a similar process to obtaining the user response phonetic representation 232. For example, a text form of the target word 204 can be used to obtain the target word phonetic representation 242 using a dictionary or a rules-based approach. Following operation 240, the flow of the method 200 can move to operation 250.

Operation 250 includes comparing the user response phonetic representation 232 and the target word phonetic representation 242 to obtain comparison data 252. In some examples, the comparison data 252 includes a score, and the operation 250 can include determining the score based on a difference between the user response phonetic representation 232 and the target word phonetic representation 242. In some examples, an initial score 254 can be determined and then modified to reach a final score 256. Where there are multiple user response phonetic representations 232 and/or target word phonetic representations 242, multiple different scores can be calculated between different pairs of the representations and a highest score can be selected as the score.

In an example, the initial score 254 can be based on whether particular parts of the phonetic representations 232, 242 match. For instance, where the target word is a consonant-vowel-consonant (CVC) word, the initial score can be broken into three components having the form [$c_1$, v, $c_2$], where $c_1, v, c_2 \in \{0, 1\}$ and where a value of 1 represents a match and a value of 0 represents that there was no match. Other kinds of configurations can be used and need not be limited to three part form or CVC form.

Where the target word phonetic representation 242 is [d, ɔ, g] ("dog") and the user response phonetic representation is [d, I, g] ("dig"), then the initial score 254 can be [1, 0, 1], which reflects that the phonetic portions representing the consonants of the target word 204 matched and that the phonetic portions corresponding to the vowel did not match. In an example, the insertion and substitution of additional phonemes can invalidate a correct phoneme. As a specific example, the target word phonetic representation 242 is [s, æ, p] ("sap") and the user response phonetic representation 232 is [s, n, æ, p] ("snap"). Because the consonants and vowel of the target word phonetic representation 242 are in the user response phonetic representation 232, the initial score 254 may be [1, 1, 1], but because of the addition of the extra phoneme "n" to the first consonant portion, the initial score 254 may be modified to set the first consonant portion to be incorrect. This change can result in the final score 256 being [0, 1, 1].

In some examples, the comparison data 252 includes a score based on the [$c_1$, v, $c_2$] representation, such as a scores calculated as:

$$s = c_1 + v + c_2 \text{ or as } s = \frac{c_1 + v + c_2}{3} \times 100.$$

The overall score for the audiometric test 202 can be the sum, average, or another calculation based on a combination of some or all of the individual scores of the comparison data 252 associated with each of the target words 204.

In some examples, the score or other comparison data 252 can be generated based on a distance between the user response phonetic representation 232 and the target word phonetic representation 242. The difference can be determined based on any of a variety of techniques, such as a Levenshtein distance, a Hamming distance, a Damerau-Levenshtein distance, or another distance technique. For example, where Levenshtein distance is used, the score or other comparison data can be the smallest number of deletions, insertions, and substitutions needed for the two representations 232, 242 to match. In some examples, a minimal-cost calculation is added that uses the knowledge that a phoneme is either a vowel or a consonant to determine the most likely edit operation. Where there are multiple transcriptions (e.g., multiple different possible phonetic representations for the target word 204 or the user response 222), all transcriptions can be compared and the best match (e.g., highest score) can be used. In some instances, the score or comparison data 252 can track or be based on changes in the use of consonants and vowels, such as by using the following edit indicators:

| Edit Type | Abbreviation |
|---|---|
| Correct Consonant | Cc |
| Correct Vowel | Cv |
| Deletion | D |
| Insert Consonant | Ic |
| Insert Vowel | Iv |
| Substitution by the same phoneme type | S |
| Substitution from vowel to consonant | Svc |
| Substitution from consonant to vowel | Scv |

The correct consonant edit type can indicate a phonetic match between a consonant portion of the user response phonetic representation 232 and the target word phonetic representation 242, such as "s" and "s". The correct vowel edit type can indicate a phonetic match between a vowel portion of the user response phonetic representation 232 and the target word phonetic representation 242, such as "a" and "a". The deletion edit type can indicate that the user response phonetic representation 232 entirely lacks a component (e.g., a consonant or vowel) of the target word phonetic representation. For instance, where the target word 204 is "dog", a user response phonetic representation 232 of [d, ɔ] ("do") can represent a deletion of a second consonant part ("g") of the target word phonetic representation 242 of [d, ɔ,g] ("dog"). The insert consonant edit type can indicate that the user response phonetic representation 232 adds a consonant part that is not present in the target word 204. For instance, where the target word 204 is "do", a user response phonetic representation 232 of [d, ɔ, g] ("dog") represents the addition of a second consonant part ("g") compared to the target word phonetic representation 242. The insert vowel edit type can indicate that the user response phonetic representation 232 adds a vowel part that is not present in the target word 204. For instance, where the target word phonetic representation 242 is [d,α,t] ("dot") and the user response phonetic representation 232 is [d,æ,t,ə] ("data"), the addition of the "ə" phoneme can be considered an insert vowel edit. The substitution by the same phoneme type edit type can indicate that the user response phonetic representation 232 swapped one phoneme for another phoneme of the same type. For instance, in the dot-data example above, the presence of "æ" instead of "α" in the user response phonetic representation 232 can represent a substitution of the same phoneme type. The substation from vowel to consonant edit type can indicate that the user response phonetic representation 232 included a consonant where the target word phonetic representation 242 included a vowel. For instance, where the target word phonetic representation 242 is [e,I,t] ("ate") and the user response phonetic representation is [k,I,t] ("kit"), the substitution of "k" for "e" can represent a substitution from vowel to consonant. The substation from consonant to vowel edit type can indicate that the user response phonetic representation 232 included a vowel where the target word phonetic representation 242 included a consonant. For instance, where the target word phonetic representation 242 is [k,I,t] ("kit") and the user response phonetic representation is [e,I,t] ("ate"), the substitution of "e" for "k" can represent a substitution from a consonant to a vowel.

Figure 3:
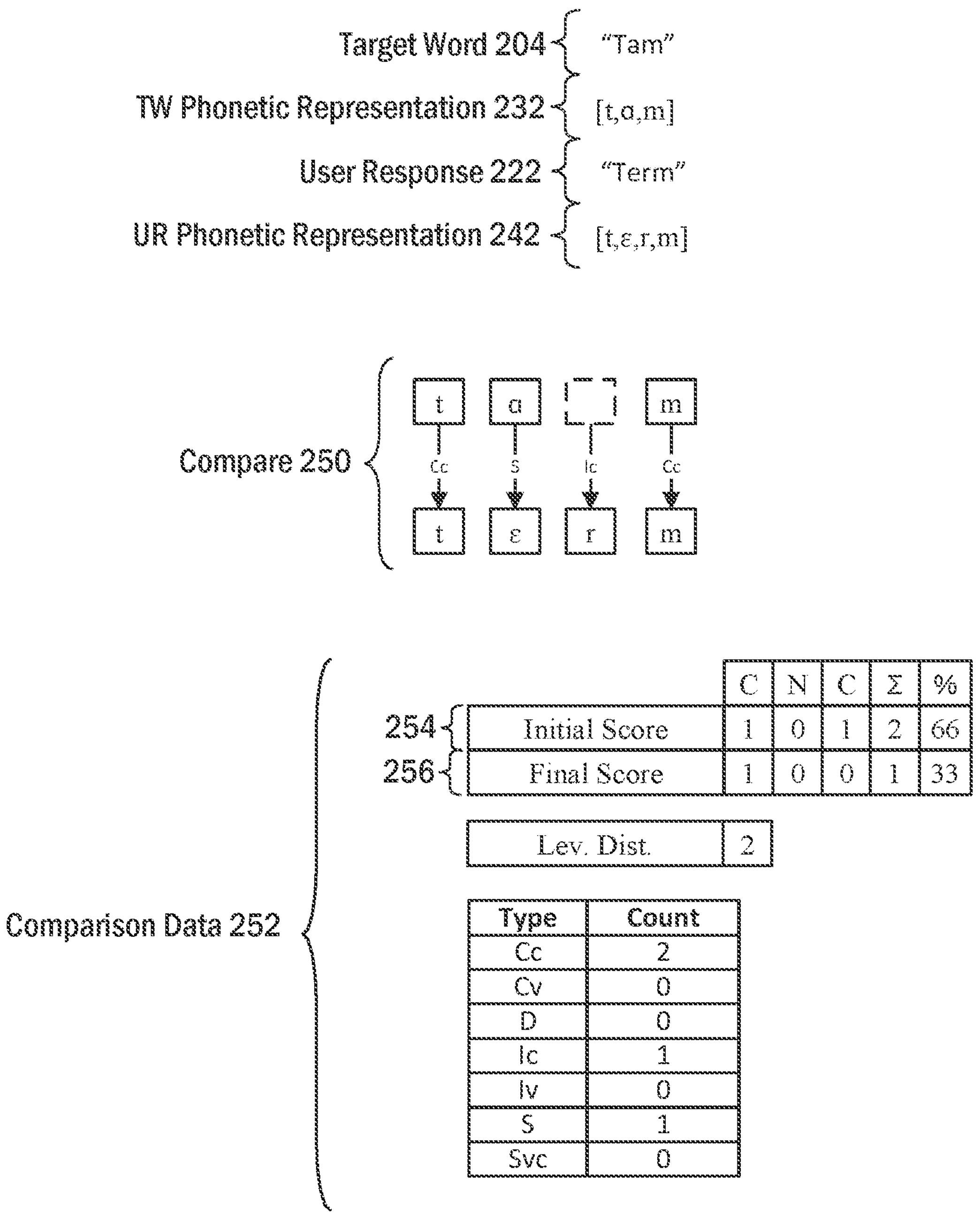
FIG. 3 illustrates an example production of a final score based on a response to a target word.
Figure 4:
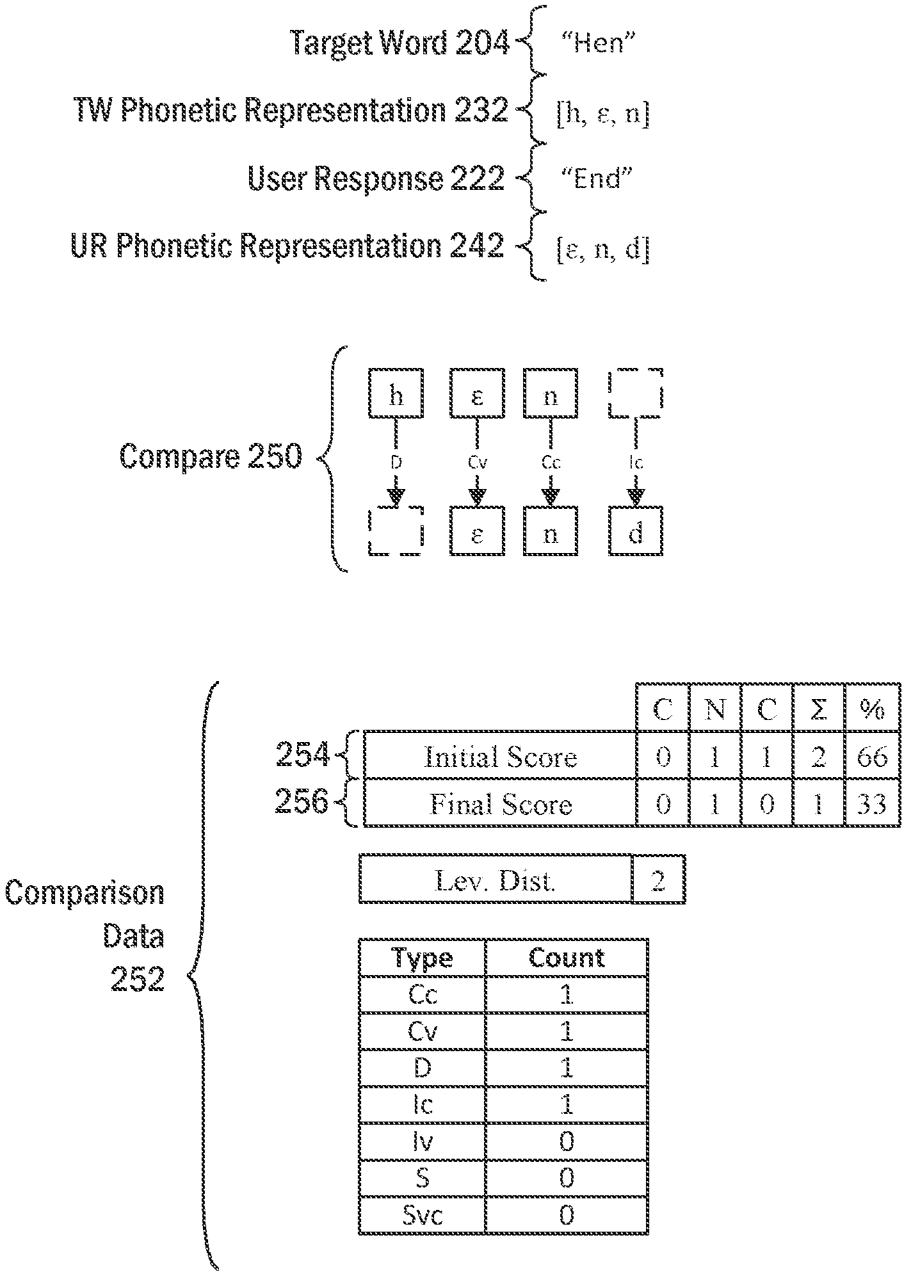
FIG. 4 illustrates another example production of a final score based on a response to a target word.

Examples of comparison data 252 resulting from the operation 250 are shown in FIGS. 3 and 4. FIG. 3 illustrates an example production of a final score 256 and other comparison data 252 based on a user response 222 to a target word 204. In this example, the target word 204 is "tam", which has a target word phonetic representation 242 of [t,α,m]. The target word 204 is provided to the user, and a user response 222 of "term" is received, which has the user response phonetic representation 232 of [t,ε,r,m]. The comparison reveals a correct consonant ("t"), a same phoneme type substitution (substituting the vowel sound "ε" for "α"), the insertion of a consonant ("r"), and a correct consonant ("m"). The comparison results in an initial score 254 of [1,0,1] because the first and last consonants match and the vowel sounds do not match. Further processing results in a final score of [1,0,0] because the last consonant was incorrect due to the insertion of "r" in addition to the correct "m". FIG. 4 illustrates another example production of a final score 256 and other comparison data 252 based on a user response 222 to a target word 204. In this example, the target word 204 is "hen" having a target word phonetic representation 242 of [h,ε,n]. The target word 204 is provided to the user, and a user response 222 of "end" is received, which has the user response phonetic representation 232 of [ε, n, d]. The comparison reveals the deletion of a consonant ("h"), a correct vowel ("ε"), a correct consonant ("n"), and the insertion of a consonant ("d"). The comparison results in an initial score 254 of [0,1,1] because the vowel and last consonant match. Further processing results in a final score 256 of [0,1,0] because the last consonant was incorrect due to the insertion of an incorrect consonant ("d") in addition to the correct consonant as part of the final consonant.

Returning to FIG. 2, as can be seen above, any of a variety of techniques can be used to compare the user response phonetic representation 232 and the target word phonetic representation 242 to generate the comparison data 252, and the comparison data 252 can include any of a variety of data. Following operation 250, the flow of the method 200 can move to operation 260. In some examples, if there are additional target words 204 in the audiometric test 202, then the flow of the method 200 can return to operation 206 for selection of a next target word 204. If there are no additional target words 204 to be provided, then the flow of the method can move to operation 260.

Operation 260 includes determining the user's ability to hear 262 based on the comparison data 252. The user's ability to hear 262 can take any of a variety of forms. In some instances, the user's ability to hear 262 can be a qualitative score, such as a sum or average of one or more scores determined in the comparison data 252. In addition or instead, the determined ability to hear 262 can include identification of particular sounds, frequencies, phonemes, syllables, parts of speech, or other aspects with which the user has difficulty hearing or understanding. In addition or instead, the ability to hear 262 can relate to an ability to hear using a particular ear or in particular conditions. For instance, an audiometric test may add particular complications to the test audio relating to particular conditions (e.g., white noise, brown noise, sounds of one or more conversations occurring, echo, reverberation, distortion, or other effects) and the ability to hear 262 can further include data regarding the conditions in which the user hears better or worse.

In some examples, the determining of the ability of the user to hear 262 is further based on the amount of time the user takes to respond to the test audio 212. For example, the method 200 can include determining an amount of time between the test audio 212 ending and beginning to receive the user response 222. The amount of time can be an indication of an amount of ease or difficulty with which the user perceived the test audio 212.

Following operation 260, the flow of the method 200 can move to operation 270.

Operation 270 includes performing a treatment action 272 based on the ability to hear 262. For instance, the treatment actions can include providing the user with a hearing device or modifying an existing hearing device of the user (e.g., adjust low frequency gains of the device responsive to vowel errors or adjusting the high frequency gains in response to errors with fricatives). In some examples, the treatment action 272 includes diagnosing the user as having a particular hearing condition.

In an example, the treatment action 272 is an action relating to the treatment of a medical condition associated with the recipient's auditory system. Various treatment actions 272 can be determined or recommended. In an example, the treatment action 272 includes reporting a performance quality of user's hearing, such as to a clinician (e.g., to help guide treatment) or caregiver (e.g., to help assure the caregiver that an auditory device of the user is functioning as intended). In an example, the treatment action 272 includes providing a metric estimating the recipient's ability to perceive particular sounds. In an example, the treatment action 272 includes recommending corrective actions.

In an example, the treatment action 272 includes recommending corrective actions (e.g., reconfiguration, reprogramming, or revising the therapy, such as by advancing to bilateral prostheses from a unilateral prosthesis). In some examples, the treatment action 272 can include recommendations or modifications for one or more auditory device settings 122 of the auditory device 120 of the user. Modifying the auditory device settings 122 can result in the modification of the ongoing treatment provided by the auditory device 120. Based on the audiometric test results 500, it can be determined that the auditory device settings 122 are sub-optimally causing auditory percepts in the recipient with respect to particular auditory input (e.g., particular phonemes or sounds) and that one or more changes to the auditory device settings 122 might be able to improve the performance of the auditory device 120. Based on the determination, information regarding the one or more changes can be provided to the recipient, a caregiver, or a clinician (e.g., by way of a report to the clinician computing device 180). In some examples, the one or more changes are automatically adopted by the auditory device 120 itself. The auditory device settings 122 are then changed, which modifies the ongoing operation of the auditory device 120. In some examples, scene-specific auditory device settings 122 are changed. For instance, the auditory device settings 122 associated with a speech mode (e.g., as determined by a scene classifier of the auditory device 120) are changed but not in other modes (e.g., music or wind modes).

The treatment action 242 can include using the ability to hear 262 or audiometric test results 500 as input to a hearing rehabilitation training program. The hearing rehabilitation program can take any of a variety of forms. For example, the hearing rehabilitation program can include the use of rehabilitation exercises, such as playlists of words having sounds that the user had trouble hearing. As a particular example, the audiometry application 116 may provide (automatically or based on clinician feedback) a user with particular exercises to perform, such as listening to a list of words starting with a particular phoneme (e.g., a particular phoneme that a hearing test indicated that the recipient had difficulty understanding).

Example Audiometric Test Results

Figure 5A:
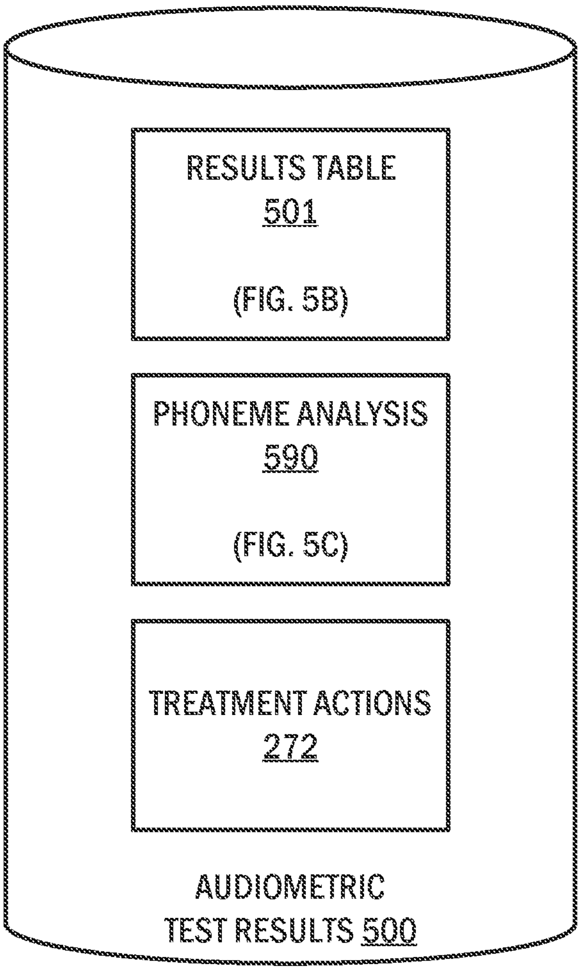
FIG. 5A illustrates example audiometric test results.

FIG. 5, which is made up of FIGS. 5A, 5B, and 5C, illustrates an example audiometric test results 500 for an audiometric test 202 (e.g., conducted using the method 200). As illustrated in FIG. 5A, the audiometric test results 500 can include a results table 501, phoneme analysis 590, and one or more treatment actions 272 that are recommended. The audiometric test results 500 can be generated, for example, as part of operations 250 and/or 260 as described above.

FIG. 5B illustrates an example implementation of the results table 501. The results table 501 can be a data table that is produced after the audiometric test 202 is provided. The results table 501 can be provided to a clinician or a program for analysis to determine an ability of the recipient to hear. The results table 501 includes ten entries 502, each corresponding to a different word-response cycle. The results table 501 further includes several fields, including a file field 510, a target word field 520, a user response field 530, a target word phoneme field 540, a user response phoneme field 550, a phoneme score field 560, a word score field 570, and a response time field 580. The file field 510 is a field describing which file (e.g., audio file) was used to produce the audio containing the target word 204. The target word field 520 describes the text of the target word 204. The user response field 530 describes the user response 222 in text form. The target word phonemes field 540 is a field that describes the target word phonetic representation 242. The user response phonemes field 550 is a field that describes the user response phonetic representation 532. As illustrated, more than one different phoneme representations can be stored in association with the phonemes fields 540, 550. The phoneme score field 560 is a field describing a phoneme score. In the illustrated example, the phoneme scores are in the three-part CVC form described above: [$c_1$, v, $c_2$], where $c_1, v, c_2 \in \{0, 1\}$. Other configurations are also possible. The word score field 570 describes a word score. In the illustrated example, the word score is a count of the matches in the phoneme score field 560. The response time field 580 is a field that describes the amount of time between the target word 204 being provided and the user beginning to provide the user response. In the illustrated example, the response time field 580 describes data in the form of milliseconds.

FIG. 5C illustrates an example implementation of the phoneme analysis data 590. In the illustrated example, the phoneme analysis data 590 includes a phoneme results data 592 and score data 594.

The phoneme results data 592 can include phoneme-specific data regarding the audiometric test 202. The phoneme results data 592 can be expressed in any of a variety of ways. In the illustrated example, the phoneme results data 592 is implemented as a table showing, for each phoneme presented during the test, how correct or incorrect the user responses were with respect to a particular phoneme. Such data can be used to, for example, help identify particular sounds that the user has difficulty hearing. Certain phonemes can tend to be produced at a higher or lower frequency than others. For instance, the phoneme "IY" as pronounced in the word "bean" is relatively higher frequency than the phoneme "OW" as pronounced in the word "hope". A high incidence of incorrect answers relating to the phoneme "IY" could indicate that the user has difficulty hearing high-frequency sounds. While a high incidence of incorrect answers relating to phonemes associated with low-frequency sounds could indicate that the user has difficulty hearing low-frequency sounds.

The score data 594 can include data regarding a score of the user for the audiometric test 202. For example, as illustrated the score data 594 can include a total phoneme score in the form of a total number of correct answers for parts of CVC words in [$c_1$, v, $c_2$] form. In addition or instead, the score data 594 can include a total word score (e.g., the total number of correct components) or a percent correct answers. In addition or instead, other data can be used.

Auditory Devices

The audiometric tests described herein can be used with any of a variety of users, including users that are recipients of one or more auditory devices 120. The auditory devices 120 can include devices relating to a recipient's sense of hearing. The auditory devices 120 can take a variety of forms including a cochlear implant, an electroacoustic device, a percutaneous bone conduction device, a passive transcutaneous bone conduction device, an active transcutaneous bone conduction device, a middle ear device, a totally-implantable auditory device, a mostly-implantable auditory device, an auditory brainstem implant device, a hearing aid, a tooth-anchored hearing device, a personal sound amplification product, other auditory prostheses, and combinations of the foregoing (e.g., binaural systems that include a prosthesis for a first ear of a recipient and a prosthesis of a same or different type for the second ear).

The audiometric tests described herein can be used to determine how well the user's auditory device 120 is functioning and whether one or more changes to the auditory device settings 122 may be beneficial.

Figure 6:
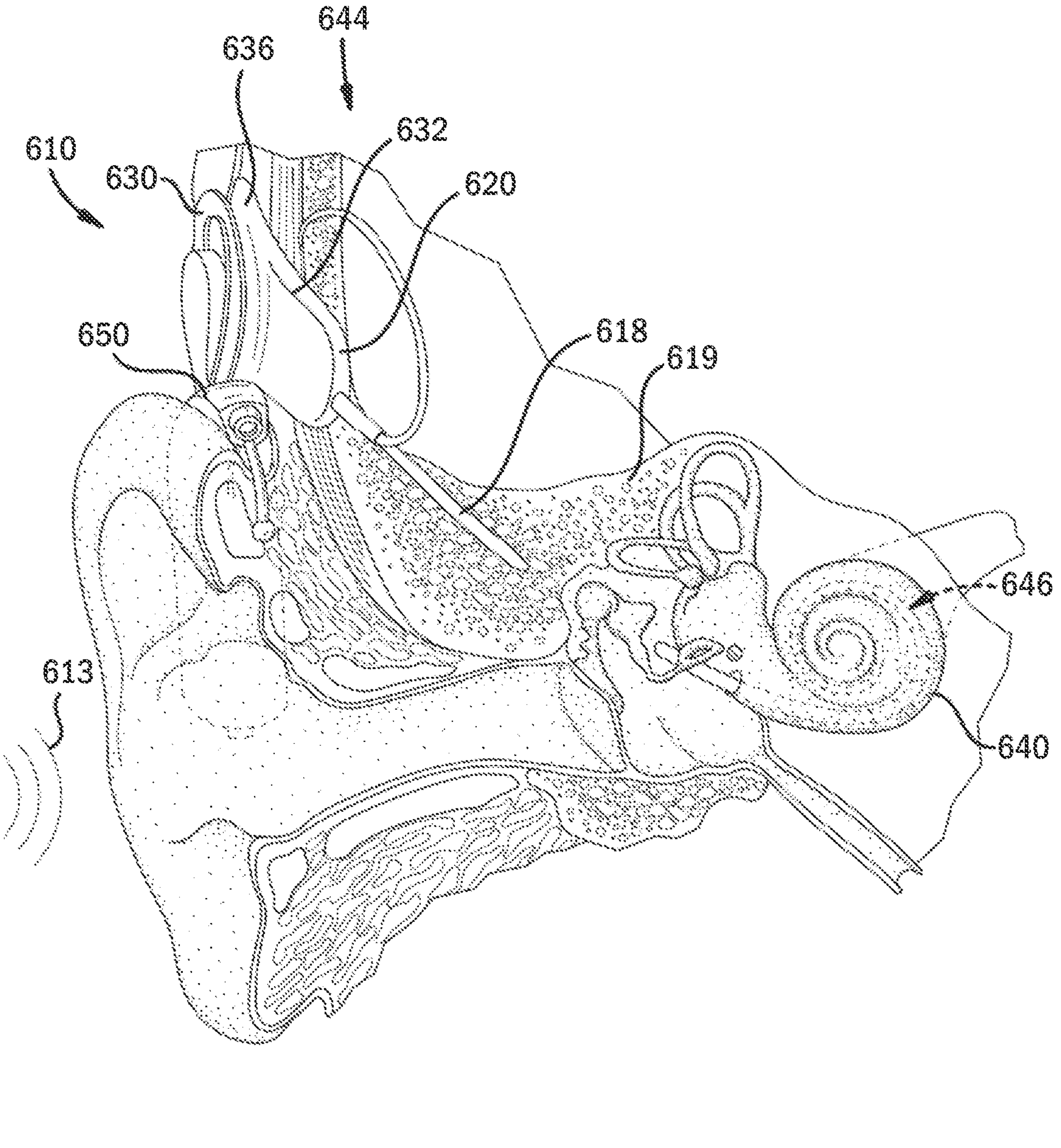
FIG. 6 illustrates an example cochlear implant system that can benefit from use of the technologies disclosed herein.
Figure 7:
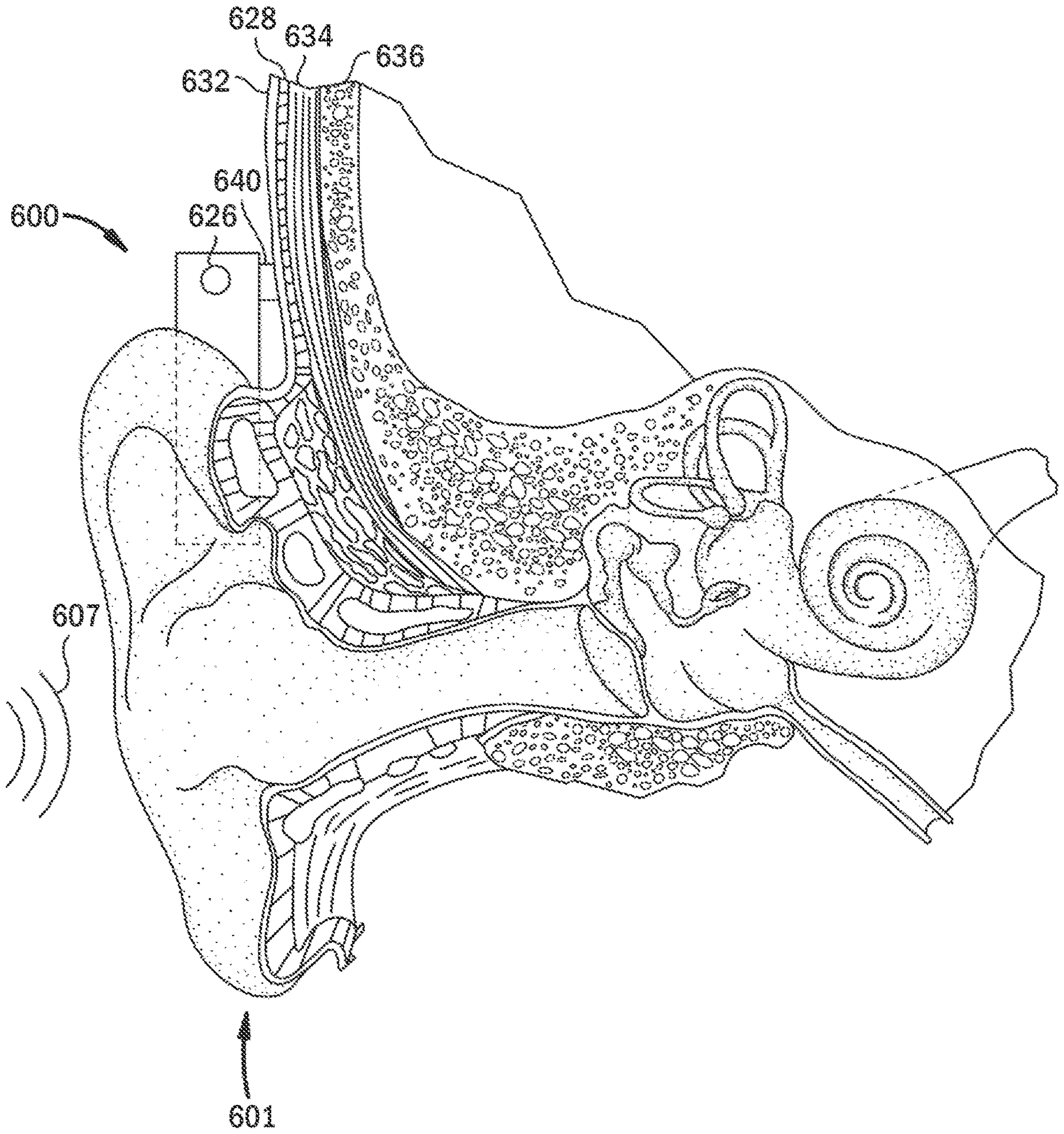
FIG. 7 is a view of an example percutaneous bone conduction device that can benefit from use of the technologies disclosed herein.

Example implementations of the auditory devices are described in more detail in FIG. 6 (showing a cochlear implant) and FIG. 7 (showing a percutaneous bone conduction device).

Auditory Devices—Cochlear Implant System

FIG. 6 illustrates an example cochlear implant system 610 that can benefit from use of the technologies disclosed herein. The cochlear implant system 610 includes an implantable component 644 typically having an internal receiver/transceiver unit 632, a stimulator unit 620, and an elongate lead 618. The internal receiver/transceiver unit 632 permits the cochlear implant system 610 to receive signals from and/or transmit signals to an external device 650. The external device 650 can be a button sound processor worn on the head that includes a receiver/transceiver coil 630 and sound processing components. Alternatively, the external device 650 can be just a transmitter/transceiver coil in communication with a behind-the-ear device that includes the sound processing components and microphone.

The implantable component 644 includes an internal coil 636, and preferably, a magnet (not shown) fixed relative to the internal coil 636. The magnet can be embedded in a pliable silicone or other biocompatible encapsulant, along with the internal coil 636. Signals sent generally correspond to external sound 613. The internal receiver/transceiver unit 632 and the stimulator unit 620 are hermetically sealed within a biocompatible housing, sometimes collectively referred to as a stimulator/receiver unit. Included magnets (not shown) can facilitate the operational alignment of an external coil 630 and the internal coil 636, enabling the internal coil 636 to receive power and stimulation data from the external coil 630. The external coil 630 is contained within an external portion. The elongate lead 618 has a proximal end connected to the stimulator unit 620, and a distal end 646 implanted in a cochlea 640 of the recipient. The elongate lead 618 extends from stimulator unit 620 to the cochlea 640 through a mastoid bone 619 of the recipient. The elongate lead 618 is used to provide electrical stimulation to the cochlea 640 based on the stimulation data. The stimulation data can be created based on the external sound 613 using the sound processing components and based on the auditory device settings 122.

In certain examples, the external coil 630 transmits electrical signals (e.g., power and stimulation data) to the internal coil 636 via a radio frequency (RF) link. The internal coil 636 is typically a wire antenna coil having multiple turns of electrically insulated single-strand or multi-strand platinum or gold wire. The electrical insulation of the internal coil 636 can be provided by a flexible silicone molding. Various types of energy transfer, such as infrared (IR), electromagnetic, capacitive and inductive transfer, can be used to transfer the power and/or data from external device to cochlear implant. While the above description has described internal and external coils being formed from insulated wire, in many cases, the internal and/or external coils can be implemented via electrically conductive traces.

Auditory Devices—Percutaneous Bone Conduction Device

FIG. 7 is a view of an example of a percutaneous bone conduction device 700 that can benefit from use of the technologies disclosed herein. For example, the sensory prosthesis settings 146 of the device 700 can be customized using one or more aspects of disclosed technology. The bone conduction device 700 is positioned behind an outer ear 701 of a recipient of the device. The bone conduction device 700 includes a sound input element 726 to receive sound signals 707. The sound input element 726 can be a microphone, telecoil or similar. In the present example, the sound input element 726 may be located, for example, on or in the bone conduction device 700, or on a cable extending from the bone conduction device 700. Also, the bone conduction device 700 comprises a sound processor (not shown), a vibrating electromagnetic actuator and/or various other operational components.

More particularly, the sound input element 726 converts received sound signals into electrical signals. These electrical signals are processed by the sound processor. The sound processor generates control signals that cause the actuator to vibrate. In other words, the actuator converts the electrical signals into mechanical force to impart vibrations to a skull bone 736 of the recipient. The conversion of the electrical signals into mechanical force can be based on the sensory prosthesis settings 146, such that different sensory prosthesis settings 146 may result in different mechanical force being generated from a same sound signal 707.

The bone conduction device 700 further includes a coupling apparatus 740 to attach the bone conduction device 700 to the recipient. In the illustrated example, the coupling apparatus 740 is attached to an anchor system (not shown) implanted in the recipient. An exemplary anchor system (also referred to as a fixation system) may include a percutaneous abutment fixed to the skull bone 736. The abutment extends from the skull bone 736 through muscle 734, fat 728 and skin 732 so that the coupling apparatus 740 may be attached thereto. Such a percutaneous abutment provides an attachment location for the coupling apparatus 740 that facilitates efficient transmission of mechanical force.

Example Computing System

Figure 8:
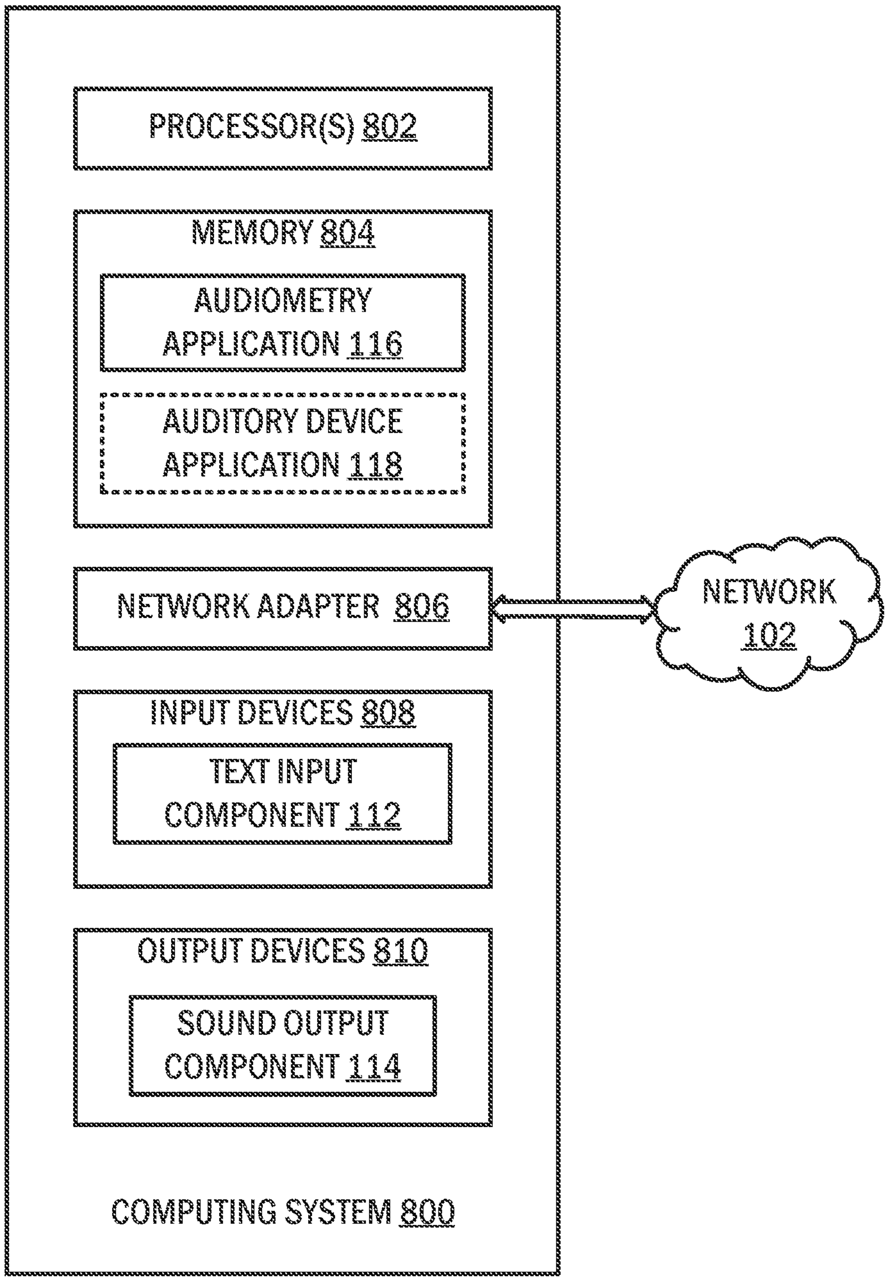
FIG. 8 illustrates an example of a computing system with which one or more of the disclosed examples can be implemented.

FIG. 8 illustrates an example of a suitable computing system 800 with which one or more of the disclosed examples can be implemented. Computing systems, environments, or configurations that can be suitable for use with examples described herein include, but are not limited to, personal computers, server computers, hand-held devices, laptop devices, multiprocessor systems, microprocessor-based systems, programmable consumer electronics (e.g., smart phones), network PCs, minicomputers, mainframe computers, tablets, distributed computing environments that include any of the above systems or devices, and the like. The computing system 800 can be a single virtual or physical device operating in a networked environment over communication links to one or more remote devices. The remote device can be an auditory device (e.g., the auditory device 120), the computing device 110, a personal computer, a server, a router, a network personal computer, a peer device or other common network node. In examples, the computing device 110 and the server 170 includes one or more components or variations of components of the computing system 800. Further, in some examples, the auditory device 120 includes one or more components of the computing system 800.

In a basic configuration, computing system 800 includes one or more processors 802 and memory 804.

The one or more processors 802 can include one or more hardware or software processors (e.g., central processing units or microprocessors) that can obtain and execute instructions. The one or more processors 802 can communicate with and control the performance of other components of the computing system 800.

The memory 804 can include one or more software- or hardware-based computer-readable storage media operable to store information accessible by the one or more processors 802. The memory 804 can store, among other things, instructions executable by the one or more processors 802 to implement applications or cause performance of operations described herein, as well as other data. The memory 804 can be volatile memory (e.g., RAM), non-volatile memory (e.g., ROM), or combinations thereof. The memory 804 can include transitory memory or non-transitory memory. The memory 804 can also include one or more removable or non-removable storage devices. In examples, the memory 804 can include RAM, ROM, EEPROM (Electronically-Erasable Programmable Read-Only Memory), flash memory, optical disc storage, magnetic storage, solid state storage, or any other memory media usable to store information for later access. In examples, the memory 804 encompasses a modulated data signal (e.g., a signal that has one or more of its characteristics set or changed in such a manner as to encode information in the signal), such as a carrier wave or other transport mechanism and includes any information delivery media. By way of example, and not limitation, the memory 804 can include wired media such as a wired network or direct-wired connection, and wireless media such as acoustic, RF, infrared and other wireless media or combinations thereof.

In the illustrated example, the system 800 further includes a network adapter 806, one or more input devices 808, and one or more output devices 810. The system 800 can include other components, such as a system bus, component interfaces, a graphics system, a power source (e.g., a battery), among other components.

The network adapter 806 is a component of the computing system 800 that provides network access. The network adapter 806 can provide wired or wireless network access and can support one or more of a variety of communication technologies and protocols, such as ETHERNET, cellular, BLUETOOTH, near-field communication, and RF (Radiofrequency), among others. The network adapter 806 can include one or more antennas and associated components configured for wireless communication according to one or more wireless communication technologies and protocols.

The one or more input devices 808 are devices over which the computing system 800 receives input from a user. The one or more input devices 808 can include physically-actuatable user-interface elements (e.g., buttons, switches, or dials), touch screens, keyboards, mice, pens, and voice input devices, among others input devices.

The one or more output devices 810 are devices by which the computing system 800 is able to provide output to a user. The output devices 810 can include, displays, speakers, and printers, among other output devices.

As should be appreciated, while particular uses of the technology have been illustrated and discussed above, the disclosed technology can be used with a variety of devices in accordance with many examples of the technology. The above discussion is not meant to suggest that the disclosed technology is only suitable for implementation within systems akin to that illustrated in the figures. In general, additional configurations can be used to practice the processes and systems herein and/or some aspects described can be excluded without departing from the processes and systems disclosed herein.

This disclosure described some aspects of the present technology with reference to the accompanying drawings, in which only some of the possible aspects were shown. Other aspects can, however, be embodied in many different forms and should not be construed as limited to the aspects set forth herein. Rather, these aspects were provided so that this disclosure was thorough and complete and fully conveyed the scope of the possible aspects to those skilled in the art.

As should be appreciated, the various aspects (e.g., portions, components, etc.) described with respect to the figures herein are not intended to limit the systems and processes to the particular aspects described. Accordingly, additional configurations can be used to practice the methods and systems herein and/or some aspects described can be excluded without departing from the methods and systems disclosed herein.

Similarly, where steps of a method are disclosed, those steps are described for purposes of illustrating the present methods and systems and are not intended to limit the disclosure to a particular sequence of steps. For example, the steps can be performed in differing order, two or more steps can be performed concurrently, additional steps can be performed, and disclosed steps can be excluded without departing from the present disclosure. Further, the disclosed processes can be repeated.

Although specific aspects were described herein, the scope of the technology is not limited to those specific aspects. One skilled in the art will recognize other aspects or improvements that are within the scope of the present technology. Therefore, the specific structure, acts, or media are disclosed only as illustrative aspects. The scope of the technology is defined by the following claims and any equivalents therein.

What is claimed is:

1. A computer-readable medium storing instructions that, when executed by one or more processors, cause the one or more processors to:

select a target word from a plurality of words of an audiometric test;

provide test audio of the target word being pronounced;

obtain a user response as text data over a user interface;

generate a user response phonetic representation of the text data;

obtain a target word phonetic representation for the target word;

compare the user response phonetic representation and the target word phonetic representation to obtain a distance between the user response phonetic representation and the target word phonetic representation;

determine an ability of a user to hear based on the distance; and modify an auditory device of the user based on the determined ability of the user to hear.

2. The computer-readable medium of claim 1, wherein the instructions executable to compare the user response phonetic representation and the target word phonetic representation to obtain the distance between the user response phonetic representation and the target word phonetic representation comprise instructions executable to:

determine a score based on the distance, wherein the user response phonetic representation is determined based on a set of phonetic transcription codes or an alphabetic system of phonetic notation.

3. The computer-readable medium of claim 2, wherein the distance is a Levenshtein distance between the user response phonetic representation and the target word phonetic representation.

4. The computer-readable medium of claim 1, wherein the instructions executable to generate the user response phonetic representation of the text data comprise instructions executable to:

perform a grapheme to phoneme conversion on the text data to generate the user response phonetic representation based on a dictionary or one or more pronunciation rules of a language.

5. The computer-readable medium of claim 1, wherein the target word is a consonant-vowel-consonant word, and wherein the instructions executable to compare the user response phonetic representation and the target word phonetic representation to obtain the distance between the user response phonetic representation and the target word phonetic representation comprise instructions executable to:

determine a number and type of edits needed to convert the user response phonetic representation to the target word phonetic representation or vice versa.

6. A method comprising:

providing, to a user, test audio that includes a target word being pronounced;

obtaining a user response from the user;

converting the user response into a user response phonetic representation;

converting the target word into a target word phonetic representation;

determining a distance between the user response phonetic representation and the target word phonetic representation;

determining an ability of the user to hear based on the distance; and modifying an auditory device of the user based on the determined ability of the user to hear.

7. The method of claim 6, wherein determining the ability of the user to hear includes:

determining particular phonemes that the user has difficulty hearing, wherein the difficulty is measured by a performance of the user on an audiometric test determined based on the distance between the user response phonetic representation and the target word phonetic representation.

8. The method of claim 6, wherein the user response includes text data, and wherein converting the user response into a user response phonetic representation includes:

performing a grapheme to phoneme conversion on the text data to generate the user response phonetic representation.

9. The method of claim 6, wherein the user response includes audio data, and wherein converting the user response into a user response phonetic representation includes:

transcribing the audio data into one or more phonemes to generate the user response phonetic representation.

10. The method of claim 6, wherein modifying the auditory device of the user based on the determined ability of the user to hear includes:

automatically modifying a setting of the auditory device of the user based on the determined ability of the user to hear.

11. The method of claim 6, wherein converting the target word into the target word phonetic representation includes:

obtaining a plurality of phonetic representations for the target word; and selecting a phonetic representation from the plurality of phonetic representations that best matches the user response phonetic representation as the target word phonetic representation.

12. The method of claim 6, wherein the user response phonetic representation is determined based on a set of phonetic transcription codes or an alphabetic system of phonetic notation, and wherein the distance is a Hamming distance or a Damerau-Levenshtein distance between the user response phonetic representation and the target word phonetic representation.

13. The method of claim 6, wherein the distance is a Levenshtein distance between the user response phonetic representation and the target word phonetic representation.

14. The method of claim 6, further comprising:

determining an amount of time between the test audio ending and beginning to receive the user response, wherein the determining of the ability of the user to hear is further based on the amount of time.

15. The method of claim 6, wherein obtaining the user response phonetic representation includes:

obtaining a plurality of phonetic representations for the user response; and selecting a phonetic representation from the plurality of phonetic representations that best matches the target word phonetic representation as the user response phonetic representation.

16. A system comprising:

a text input component;

a sound output component;

one or more processors; and memory storing instructions that, when executed by the one or more processors, cause the one or more processors to:

provide, via the sound output component, test audio that includes a target word being pronounced;

obtain text data from the text input component;

generate a user response phonetic representation of the text data;

obtain a target word phonetic representation for the target word;

compare the user response phonetic representation and the target word phonetic representation to obtain a distance between the user response phonetic representation and the target word phonetic representation;

determine an ability of a user to hear based on the distance; and modify an auditory device of the user based on the determined ability of the user to hear.

17. The system of claim 16, further comprising:

a first computing device including:

the sound output component;

the text input component, wherein the text input component is at least one of a physical keyboard or a virtual keyboard;

the one or more processors; and the memory, wherein the memory further stores instructions that, when executed, cause the one or more processors to:

obtain the test audio from a second computing device remote from the first computing device.

18. The system of claim 17, wherein the first computing device is a consumer computing device and wherein the second computing device is a server.

19. The system of claim 16, wherein the sound output component is wirelessly-connected to the one or more processors, wherein the user response phonetic representation is generated by performing a grapheme to phoneme conversion on the text data based on a set of phonetic transcription codes or an alphabetic system of phonetic notation, and wherein the distance is determined based on one or more edit indicators associated with the user response phonetic representation or the target word phonetic representation.

20. The computer-readable medium of claim 1, wherein modifying the auditory device of the user based on the determined ability of the user to hear includes:

adjusting a frequency gain of the auditory device of the user.

* * * * *